US008709461B2

(12) United States Patent
Parkar et al.

(10) Patent No.: US 8,709,461 B2
(45) Date of Patent: Apr. 29, 2014

(54) PRESERVATION OF LIQUID FOODS

(76) Inventors: Zeba Parkar, Minneapolis, MN (US); James Economy, Urbana, IL (US); Abdul Samad, Thane (IN)

( * ) Notice: Subject to any disclaimer, the term of this patent is extended or adjusted under 35 U.S.C. 154(b) by 0 days.

(21) Appl. No.: 13/298,292

(22) Filed: Nov. 17, 2011

(65) Prior Publication Data

US 2012/0128751 A1 May 24, 2012

Related U.S. Application Data

(60) Provisional application No. 61/458,155, filed on Nov. 18, 2010.

(51) Int. Cl.

| | |
|---|---|
| ***A01N 25/08*** | (2006.01) |
| ***A01N 59/16*** | (2006.01) |
| ***A01N 25/34*** | (2006.01) |
| ***A01P 1/00*** | (2006.01) |
| ***B05D 1/18*** | (2006.01) |
| ***B05D 3/00*** | (2006.01) |
| ***B05D 3/02*** | (2006.01) |
| ***B82Y 30/00*** | (2011.01) |

(52) U.S. Cl.
USPC ........... 424/409; 424/618; 427/379; 977/773; 977/902

(58) Field of Classification Search
None
See application file for complete search history.

(56) References Cited

U.S. PATENT DOCUMENTS

| | | | | |
|---|---|---|---|---|
| 6,030,632 | A * | 2/2000 | Sawan et al. | 424/405 |
| 2005/0129742 | A1 * | 6/2005 | Bringley et al. | 424/443 |
| 2005/0224417 | A1 * | 10/2005 | Wien et al. | 210/681 |

OTHER PUBLICATIONS

Gordon Nangmenyi, Wei Xao, Sharifeh Mehrabi, Eric Mintz, and James Economy. Bactericidal activity of Ag nanoparticle-impregnated fibreglass for water disinfection. Journal of Water and Health, Jul. 4, 2009, pp. 657-663.*

* cited by examiner

*Primary Examiner* — Brian Gulledge
*Assistant Examiner* — Michael P Cohen

(57) ABSTRACT

Anti-spoilage inserts and methods are provided for inhibiting the spoilage of liquid foods.

18 Claims, 2 Drawing Sheets

PRESERVATION OF LIQUID FOODS

CROSS-REFERENCE TO RELATED APPLICATIONS

This application claims the benefit of the filing date of the U.S. provisional patent application Ser. No. 61/458,155, filed on Nov. 18, 2010, the disclosure which is herein incorporated by reference.

FIELD

Apparatus and methods for the preservation of substantially liquid foods are provided herein. More specifically, anti-spoilage inserts and methods for inhibiting the spoilage of milk are provided.

BACKGROUND

Milk is rich in nutrients, and hence is prone to rapid spoilage, including microbial spoilage. Milk spoilage is associated with an increase in bacterial populations, microbial activity, or enzymatic activity. Spoilage can occur when enzymes produced by micro-organisms degrade nutrients in milk such as carbohydrates, proteins, and fats, producing undesirable end products. Further, because of the degradation of constituents, such milk becomes more susceptible to microbial contamination.

Microbial or enzymatic activity can lead to the production of lactic acid. The increase in acidity can cause precipitation and coagulation of proteins such as casein, causing curd formation. Once curd formation is initiated, the entire amount of milk can curdle within 24 hours. In a similar manner, spoilage in other liquids foods or substantially liquid food, for instance, fruit juices or soy milk, occurs due to microbial and enzymatic activity.

In developing countries, millions of small-scale farmers depend on only one or two dairy animals to supplement their livelihood. These farmers typically can collect only small amounts of milk from the animals they own. They rely on co-operative collection centers to purchase the milk on a daily basis. The farmers often travel significant distances to transport milk from their source to co-operative collection centers, where the milk is refrigerated. Multiple trips may be needed every day. Further, in many countries, the rate of spoilage of milk is higher due to the tropical climate, which tends to encourage microbial activity because of higher ambient temperatures. Most of the subsistence farmers in such countries cannot afford refrigeration. This results a significant decrease in milk production due to spoilage.

The typical amount of time required to transport the milk from the farmer to the collection center can range from 2 to 12 hours or even more. Milk that is not refrigerated can begin to spoil because of microbial or enzymatic activity, leading to undesirable changes such as curdling. Once curdling begins, a large volume of milk is spoiled and cannot be recovered.

Developing countries in particular produce more than 300 million tons of milk per year. However, due to the inefficient process, approximately 10% of the milk production is lost due to milk spoilage in countries that face electricity shortages in rural areas. This translates to several million dollars worth of milk that spoils due to less than optimal conditions.

Even when refrigeration is available as a method for preservation, milk often has a limited shelf life. Techniques like pasteurization and ultra-high-temperature (UHT) processing can extend the life of milk. However, pasteurized milk still needs to be refrigerated to prolong its keeping quality. UHT processed milk does not need refrigeration only till the integrity of the package is maintained. Once the package or container of UHT milk is opened, it needs to be refrigerated.

Thus, the shelf-life of processed milk often depends on refrigeration facilities available. In case of any disruption such as equipment failure or power failure that prevents refrigeration, milk spoilage is hastened.

Though chemical additives can be used to preserve beverages like fruit juices, no additives can be used to preserve milk because of government regulations and consumer preferences.

Calves are often fed milk that is kept at ambient temperatures in feeding pans. Due to risk of spoilage of milk, the feeding pans are required to be replenished 2-3 times in a day which becomes cost prohibitive. Even during this time there is rapid growth of pathogenic bacteria in stored milk which can be harmful to calves. If the shelf-life of milk/milk replacers in calf feeding pans can be increased and the growth of bacteria can be inhibited, it would improve calf management practices.

Hence a need exists for a low-cost technology for the preservation of milk that does not rely on refrigeration or additives. It is additionally desirable that alternative technology developed to preserve milk or extend its shelf life does not require alterations to current storage, transport, or processing equipment.

BRIEF SUMMARY

One embodiment provides an anti-spoilage insert and a method for the inhibition of microbial spoilage of a substantially liquid food. In an embodiment, silver is deposited on a substrate by immersing the substrate in a silver nitrate solution for a predetermined period of time. In another embodiment, the substrate is made of glass fabric. In yet another embodiment, the silver is deposited on the substrate in the form of nanoparticles. In an embodiment, an anti-spoilage insert that inhibits microbial activity in substantially liquid foods includes silver deposited on a substrate. In an embodiment, a silver-deposited substrate is immersed in a substantially liquid food to inhibit microbial activity in the substantially liquid food.

DETAILED DESCRIPTION OF THE INVENTION

Figure 1:
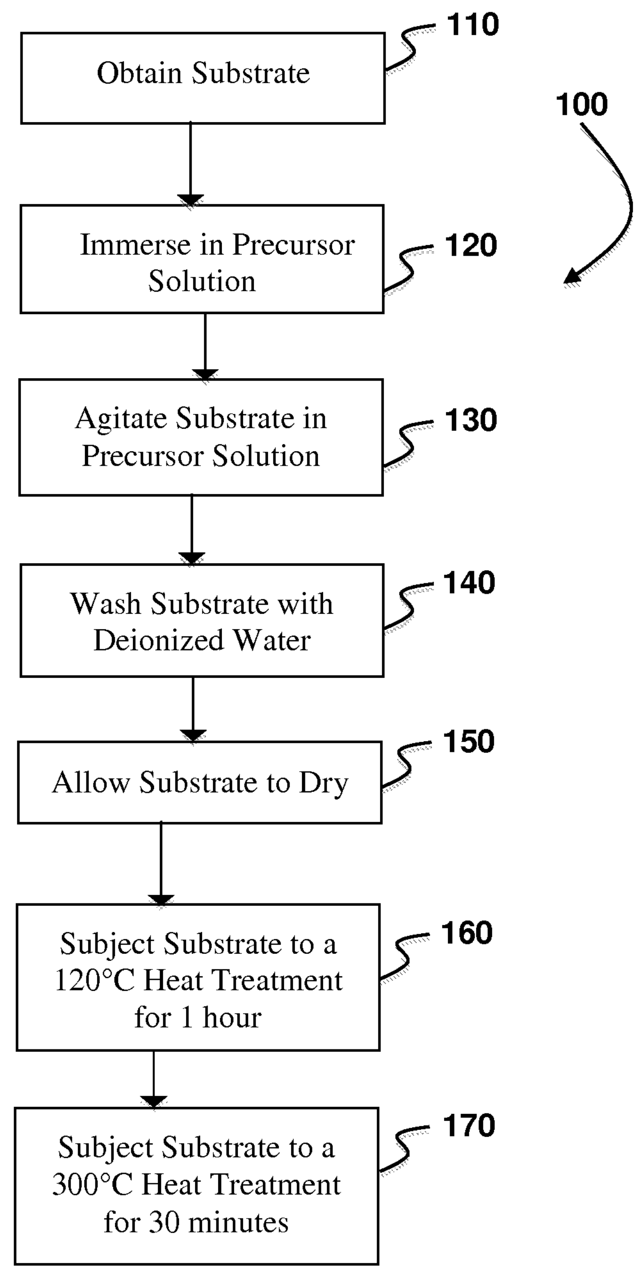
FIG. 1 illustrates a flow chart of an embodiment of a method utilized for producing an anti-spoilage insert that inhibits the spoilage of substantially liquid foods according to the present invention.

Silver is known to have antimicrobial activity against a wide spectrum of microorganism. It has the ability to kill or inhibit gram-positive and gram-negative bacteria, viruses, fungi and yeasts. Silver has been used in soap, wound dressings, textiles, and various biomedical devices as an anti-bacterial device. Silver may suppress the growth of microorganisms or their activity. The efficiency and effectiveness of silver is enhanced when silver is used in the form of nanoparticles. Nanoparticles, as the term is used herein, include particles that are substantially smaller than 500 nm in size, preferably, smaller than 250 nm and most preferably, smaller than 100 nm.

The effectiveness of silver can depend on the substrate on which silver is deposited. Substrate, as the term is used herein, includes materials such as fiberglass, clay, or carbon or any material that is capable of having particles deposited on them, or any combination of such materials.

The term substantially liquid food as used herein, is a liquid food, including but not limited to, milk or any other food that is substantially liquid, such as colostrum or dairy products. The term milk refers to liquid food that is produced by mammals, such as goats, sheep, camel, cows, buffalos, and humans or any other mammals.

In an embodiment, the substrate of the anti-spoilage insert may comprise materials on which metals can be deposited, such as, but not limited to, wood, wood-pulp, cellulose, non-woven polyethylene, non-woven polypropylene, silica, alumina, gelatin, fabric, agar, fiberglass, clay, carbon, or any combination thereof.

In an embodiment, the substrate of the anti-spoilage insert comprises a substrate on which silver is deposited.

In another embodiment the substrate of the anti-spoilage insert comprises a substrate on which silver particles are deposited.

In an embodiment, the anti-spoilage insert may additionally, or optionally, comprise substrate in the form of microscopic or macroscopic granules of various shapes and sizes, or a solid body of various shapes and sizes, or pulverized particles, or any combinations thereof.

In an embodiment, the anti-spoilage insert may additionally, or optionally, be mounted on or at the end of a wire, a shaft, a stick, a thread or any material as convenient or preferable.

In an embodiment, the anti-spoilage insert may comprise substrate contained in pouches or bags or enclosures made of paper, cloth, or plastic, which may allow the substantially liquid food to diffuse into the pouches or bags or enclosures and come partially or wholly in contact with the substrate.

In an embodiment, the anti-spoilage insert may additionally or optionally comprise an attachment element directly or indirectly connected to the anti-spoilage insert.

In an embodiment, the attachment element may include but is not limited to a hook, a clasp, a bent structure, a connecting structure, a fastener, or any combination thereof.

In an embodiment, the granular or pulverized anti-spoilage material may be coated on paper, cloth, or plastic and pasted on the inner wall of pouches or bags or enclosures which may allow the substantially liquid food to partially or wholly be in contact with the anti-spoilage film.

While various embodiments are described in the drawings and description, the present disclosure is only an exemplification and is not intended to limit the invention to the specific embodiments illustrated.

FIG. 1 illustrates a flow chart of a method for producing an anti-spoilage insert that inhibits spoilage in substantially liquid foods. In an embodiment, the method 100 for producing an anti-spoilage insert deposits a predetermined amount of silver in the form of nanoparticles on the substrate.

In step 110, the substrate is obtained. In one embodiment, the substrate is fiberglass, for example, fiberglass derived from continuous chopped nonwoven fiberglass with a polyvinyl alcohol binder.

In step 120, the substrate is immersed in a precursor solution. The precursor solution contains a predetermined amount of silver salts and deposits silver particles onto the substrate, thus creating an anti-spoilage insert.

In an embodiment, the silver salt in the precursor solution is silver nitrate. The concentration of the precursor solution may be controlled depending on the desired extent of silver deposition on the substrate. The silver content on the substrate varies based on the immersion time of the substrate in the precursor solution. In one embodiment, the precursor solution in which the substrate is immersed contains silver nitrate, $AgNO_3$. Therefore, silver is deposited on the substrate. In another embodiment, the precursor solution comprises 0.001 to 1.0 M silver nitrate. In another embodiment, the concentration of silver salt in the precursor solution is chosen in order to produce an anti-spoilage insert wherein the weight of the silver per g of the substrate is more than 0.01 mg. In yet another embodiment, the concentration of silver salt in the precursor solution is chosen in order to produce an anti-spoilage insert wherein the weight of silver per g of the substrate is more than 0.1 mg.

In an embodiment, the concentration of silver salt in the precursor solution is chosen in order to produce an anti-spoilage insert wherein the weight of the silver per g of the substrate is more than 1 mg. In another embodiment, the concentration of silver salt in the precursor solution is chosen in order to produce an anti-spoilage insert wherein the weight of silver per g of the substrate is more than 10 mg.

In step 130, the substrate is immersed, in the precursor solution, preferably accompanied by agitation. In one embodiment, this form of agitation occurs at 150 RPM for one hour in a commercial shaker.

In step 140, the substrate is removed and washed with deionized water.

In step 150, the substrate is dried. In an alternative embodiment, step 150 includes drying the substrate by leaving the substrate overnight in a laboratory hood.

In step 160, after the substrate is fully dried, it is heated. In an alternative embodiment, the heat treatment subjects the substrate to 120° C. for 1 hour.

In step 170, the substrate is heated again. In an alternative embodiment, the second heat treatment subjects the substrate to 300° C. for 0.5 hour.

In another embodiment of the invention, the heat treatment in step 160 and in step 170 is carried in the presence of an inert gas. In an embodiment of the invention, the inert gas is nitrogen.

In an embodiment, the inert gas may also include but is not limited to Helium (He), Neon (Ne), Argon (Ar), Krypton (Kr), Xenon (Xe), or any other inert gas or any combination thereof.

In an embodiment of the invention, the anti-spoilage insert formed by the method 100 is a glass fabric that is deposited with silver nanoparticles. In another embodiment of the invention, the substrate is fiberglass that has been produced, for example, from chopped nonwoven fiberglass with a polyvinyl alcohol binder. In yet another embodiment, the silver particles are nanoparticles.

In an embodiment, the anti-spoilage insert formed by the method 100 comprises a glass fabric that is deposited with silver nanoparticles. In another embodiment, the substrate is fiberglass that has been produced, for example, from chopped nonwoven fiberglass with a polyvinyl alcohol binder. In yet another embodiment, silver is in the form of nanoparticles.

In one or more embodiments of the present invention, the shape of the substrate may be altered in order to achieve enhanced surface area. For example, the shape of the substrate may be rectangular, allowing for more contact area with a substantially liquid food. In contrast, the substrate may be in the shape of a square, or any other geometrical shape. The substrate may take on the form of a three-dimensional shape if it is wound, for example, into a cylinder or box.

In an alternative embodiment, the substrate is flexible. A flexible substrate allows for easier adherence to a container. It also allows for movement of the substrate when the container containing the substantially liquid food is shaken, stirred, or shifted.

Alternatively, the substrate may be rigid, therefore not allowing any motion to disturb the shape of the substrate.

In one or more embodiments, the anti-spoilage insert may contain an attaching element that allows it to attach to a container. Attaching the substrate to the interior surface of the container ensures that the anti-spoilage insert is in contact with the substantially liquid food at all times. In an embodiment, the anti-spoilage insert is attached to the container such that it is fully immersed in the substantially liquid food.

An anti-spoilage insert according to one or more embodiments contains substrate through which the liquid is able to pass, thus coming into contact with silver not only on the surface of the substrate medium but also in between the fibers. Allowing fluid to pass through the substrate allows for increased interaction between the silver and the substantially liquid food. This increased interaction provides more opportunity for contact between the silver and every part of the fluid.

In alternative embodiments, the substrate may be closely packed together thus inhibiting the flow of substantially liquid food through the substrate. Eliminating the flow of substantially liquid food decreases the chance of nanoparticles or other forms of silver on the substrate from detaching due to movement of the substantially liquid food.

In alternative embodiments of the invention, the substrate may be closely packed together thus inhibiting the flow of beverage through the substrate. Eliminating the flow of beverage decreases the chance of particles on the substrate from detaching due to movement of the beverage, thus reducing the possibility of the leaching of particles into the milk.

An alternative embodiment includes an anti-spoilage insert that is reusable following being rinsed by another liquid, such as water. For example, when a user has reached a location in which the liquid in the container is capable of being refrigerated and no longer needs to use the anti-spoilage insert, the user may remove the anti-spoilage insert, rinse it with deionized water, and reuse the anti-spoilage insert in another container or the same container for another batch of substantially liquid food.

In alternative embodiments, the container may be composed of many different materials, including but not limited to metal, alloy, plastic, thermoplastic, thermosetting polymer, bakelite, bioplastics, wood, mud, terracotta, clay, enamel, porcelain, pottery, glass, ceramic, or any combination thereof. The container may contain a slot for attaching the anti-spoilage inserts prior to or after pouring substantially liquid food into the container.

In an embodiment, the container contains a mechanism or device for circulation of the substantially liquid food within interior improve contact with the silver deposited on the substrate. In another embodiment, the container may contain a mechanism or device that moves the anti-spoilage insert within the interior allowing for the substantially liquid food to be circulated in addition to moving the anti-spoilage insert through the liquid. In an alternate embodiment, the container may be manually shaken or moved to agitate the substantially liquid food. In another embodiment, the container may contain a mechanism that allows manual movement of the anti-spoilage insert within the substantially liquid food.

In an alternative embodiment, the beverage in the container is milk.

In an embodiment, the anti-spoilage insert comprises a fiberglass substrate with silver deposited on it. Silver may be deposited in the form of nanoparticles that may be greater than 10 nm and less than 500 nm. In an alternate embodiment, the fiberglass that the substrate is composed of may be derived from continuous chopped nonwoven fiberglass with polyvinyl alcohol binder.

In various embodiments, the anti-spoilage insert is reusable. A reusable anti-spoilage insert is an anti-spoilage insert that may be used in multiple different containers, in multiple substantially liquid foods. The anti-spoilage insert may be reused following a thermal process treatment or a rinse with deionized water.

Figure 2:
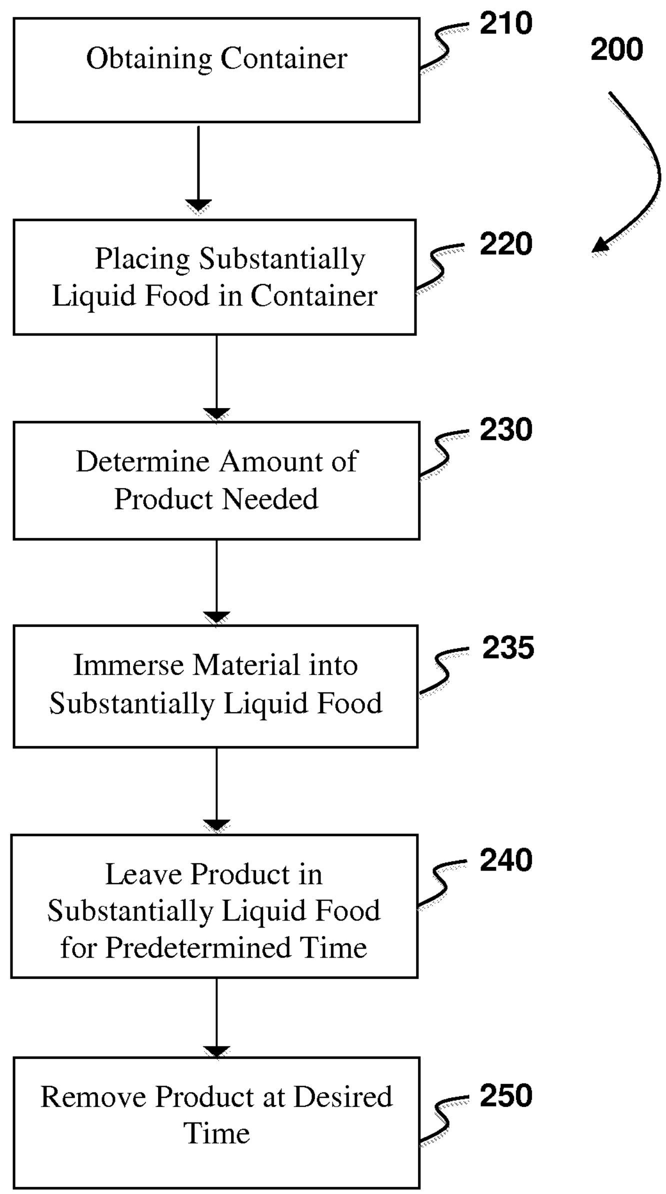
FIG. 2 illustrates a flow chart of an embodiment of a method for the inhibition of spoilage of a substantially liquid food using an anti-spoilage insert according to the present invention.

FIG. 2 illustrates a flow chart of a method 200 for inhibiting spoilage in a substantially liquid food using an anti-spoilage insert according to an embodiment.

At step 210, a container for holding a predetermined amount of substantially liquid food is obtained. In alternative embodiments, the container may be composed of, but not limited to, metal, glass, or ceramic. In an embodiment, the container is a milk canister used to transport or store milk.

In step 220, the substantially liquid food to be preserved poured into the container. The volume of substantially liquid food is measured before or after pouring into the container. In an alternative embodiment, the substantially liquid food may be pre-poured into the container when the container is obtained. In such circumstances, step 220 may be skipped.

At step 230, the amount of anti-spoilage insert is determined based on the volume of substantially liquid food in the container. In an embodiment, the anti-spoilage insert contains a weight of silver on the substrate that exceeds 0.05% on 1 mg of substrate per mL of the volume of substantially liquid food. In additional embodiments, the anti-spoilage insert contains a weight of silver on the substrate that exceeds 0.05% on 2 mg or 4 mg of substrate per mL of the volume of substantially liquid food.

At step 235, the anti-spoilage insert is substantially immersed in the substantially liquid food in the container. In an alternative embodiment, the container may have the anti-spoilage insert attached to the interior of the container or built into the container itself. Therefore, the immersion of the anti-spoilage insert into the substantially liquid food may occur as the substantially liquid food is poured into the container.

In step 240, the anti-spoilage insert is immersed in the substantially liquid food for a predetermined period of time. The silver on the substrate begins to interact with the substantially liquid food and release silver ions into the substantially liquid food. In an embodiment, the silver is in the form of silver nanoparticles, and the anti-spoilage insert is immersed in a dairy substantially liquid food such as milk. The silver ions inhibit microbial activity and inhibit spoilage of the dairy substantially liquid food. In an embodiment, the silver ions inhibit bacteria that are responsible for producing lactic acid. By eliminating or reducing the production of lactic acid, the process of curdling that leads to spoilage is significantly slowed down or inhibited.

In an embodiment, the anti-spoilage insert is immersed as long as spoilage is to be inhibited. In another embodiment, the anti-spoilage insert is immersed for a predetermined period of time in which a predetermined concentration of silver ions is attainted in the milk, after which the anti-spoilage insert is removed from the substantially liquid food. In another alternative embodiment, the interaction between the anti-spoilage insert and the substantially liquid food is enhanced by agitating the substantially liquid food within the container. Agitation may occur in several different ways, including a mechanical mixing device attached to the container, shaking the container, stirring the substantially liquid food within the container, or moving the anti-spoilage insert through the substantially liquid food.

At step 250, the anti-spoilage insert is removed from the substantially liquid food after a predetermined period of time has elapsed. In an embodiment, the anti-spoilage insert is removed from the substantially liquid food when refrigeration of the substantially liquid food is possible or the substantially liquid food is consumed. In another embodiment, the substantially liquid food is removed or poured out from the container leaving the anti-spoilage insert in the container for future use. In various embodiments, the predetermined period of time may last for a specified number of minutes, a specified number of hours, or specified number of days.

EXAMPLES

Example 1

Preparation of Anti-Spoilage Insert

The fiberglass substrates for the FG/Ag system were derived from continuous chopped nonwoven fiberglass with a polyvinyl alcohol (PVA) binder (E-glass, 6.5 μm diameter, porosity 562 cfm ft-2 @ 0.5" H2O, tensile strength [ASTMD-2101] 3450 MPa, Craneglas® 230, Crane Nonwovens, Dalton, Mass.). Lab grade deionized water was used for making solutions. Fiberglass was immersed in a 0.05 M AgNO3 solution and agitated at 150 RPM for 1 hour in a Tekmar VXR shaker (Janke & Kunkel, Staufen, Germany). The fiberglass was then removed and washed with deionized water, hang dried in the hood overnight and heat treated at 120° C. for 1 hour and at 300° C. for 30 minutes to obtain an anti-spoilage insert in the form of a silver-loaded glass fabric.

Example 2

Analysis of Silver Particles

The morphology of the silver-loaded glass fabric was characterized using a Hitachi S-4800 High Resolution Scanning Electron Microscope (SEM). A layer of Au—Pd was sputtered on the sample to avoid charging before SEM analysis. SEM analysis revealed the deposition of silver particles ranging from 5-100 nm on the glass fiber. Increase in the weight of the fiberglass was used to calculate the silver content. This was confirmed by measuring the Ag content by digesting samples in hot hydrofluoric acid (HF) solution followed by elemental analysis with an inductively coupled plasma mass spectrophotometer (ICP/MS) (Perkin Elmer/Sciex Elan-DRC, Waltham, Mass.). The leaching of silver into milk was characterized by measuring the silver content before and after the experiment. The silver particles were 0.05% by weight of the glass fiber as measured by ICP/MS.

Example 3

Observation of Anti-Spoilage Activity in Model Culture

Luria-Bertani (LB) medium containing (per liter) 10 g of tryptone, 5 g of yeast extract and 10 g of NaCl was used. *Escherichia Coli* strain AB1157 in LB medium was used as a model system for studying the effect of silver-loaded glass fabric on bacteria in milk. Cultures were grown with vigorous shaking at 37° C. To ensure that cells were growing exponentially during the experiment, the cultures were grown from OD600 of 0.005 to OD600 of 0.1 aerobically when shaking. The cultures were diluted to around 1E6 cfu/ml (OD600 of about 0.005) in 80 ml LB solution. 0.1 mg/ml of silver-loaded glass fabric was dipped in 40 ml of these spiked LB solution. Samples were taken out at 0.5, 1, 2, 4, 8, 12, 16, 20, 24 hours and diluted in LB medium and plated to obtain viable bacterial counts. Control was used a comparison throughout the experiment. Growth inhibition of bacteria was observed in presence of silver-loaded glass fabric. There was 10 orders of magnitude growth of *E. Coli* compared to just 2 orders of magnitude in the presence of silver-loaded glass fabric. $OD_{600}$ also showed drastic growth of control over 24 hours.

Example 4

Observation of Anti-Spoilage Activity in Milk

Fresh unpasteurized milk (somatic cell count ~200000) was obtained from the dairy farm at the University of Illinois for studying the effect of silver-loaded glass fabric. About 20 ml of milk was stirred at 100 rpm at 37° C. for 72 hours with 4 mg/ml of silver-loaded glass fabric and the time required for curdling and the pH were recorded after 72 hours. Milk did not show any curdling even after 72 hours at 37° C. whereas the control curdled after 30 hours. pH of milk at kept at 37° C. for 72 hours was 5.47 comparable to refrigerated milk for the same duration of time (pH=5.59).

Example 5

Alternative Method for Preparation of Anti-Spoilage Inserts

1% stock solution of sodium citrate was made by dissolving 1 gm of sodium citrate in 100 ml of deionized water. 20 ml of 1% solution of the 1% sodium citrate solution made earlier is taken and is dissolve in 80 ml deionized water. The non-woven PET sheets are dipped in this solution for 10 minutes. In the meantime, a bottle containing silver 0.05M nitrate solution is heated at 100° C. for 30 minutes. The tea bags are dipped one by one in the hot silver nitrate solution and left dipped inside the bottle for 5 minutes. The sheets are then removed from the bottle and hung to dry them in the oven at 70° C. for 30 minutes. Using around 5-20 $cm^2$ of these sheets made from tea bags in pasteurized or raw goat milk can keep the milk fresh for approximately 3 days at room temperature.

Example 6

Another Alternative Method for Preparation of Anti-Spoilage Inserts

1% stock solution of sodium citrate was made by dissolving 1 gm of sodium citrate in 100 ml of deionized water. In the meantime, a bottle containing 0.05M silver nitrate solution is placed in the oven for 30 minutes, pre-set at 100° C. After 30 minutes, the bottle is removed from the oven and non-woven PET sheets are dipped one by one in the hot silver nitrate solution. To this, 2 ml of 1% sodium citrate solution is added drop-wise in silver nitrate. The non-woven PET sheets are then removed and hung to dry in the oven at 70° C. for 30 minutes.

Example 7

Method for Preparing Anti-Spoilage Insert Using Cellulosic Substrate

1% stock solution of sodium citrate was made by dissolve 1 gm of sodium citrate in 100 ml of deionized water. 20 ml of 1% solution made above is dissolved in 80 ml of deionized water. The filter paper strips (cellulose fabric) are dipped in this solution for 10 minutes. In the meantime, a bottle containing 0.05M silver nitrate solution is preheated to 90° C. for 30 minutes. After 30 minutes, the bottle is removed from the oven. The filter paper strips (cellulose fabric) are dipped one by one in the hot silver nitrate solution. It is left to sit in the bottle for 5 minutes. The filter paper strips (cellulose fabric) are air dried or dried in the oven at 60° C. for 1 hour.

Example 8

Anti-Spoilage Insert Preventing Milk Spoilage

15 $cm^2$ of the anti-spoilage insert made from glass fabric was inserted in 200 ml of pasteurized milk which was kept at 40° C. An additional known volume of pasteurized milk was observed as a control sample. The anti-spoilage insert was not immersed in the control sample. The initial pH of the milk was 6.664. After 24 hours, the control had partly curdled (ph<5.7), while the sample with anti-spoilage insert had a pH of 6.662. After a period of 48 hours, the control had completely curdled and the sample with anti-spoilage insert had a pH of 6.559. Thus the milk without the anti-spoilage insert was curdled, while the milk with anti-spoilage insert exhibited only a minor change in the pH.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used in this specification, specify the presence of stated features, integers, steps, operations, elements, or components, but do not preclude or rule out the presence or addition of one or more other features, integers, steps, operations, elements, components, or groups thereof.

The process steps, method steps, protocols, or the like may be described in a sequential order, such processes, methods, and protocol, may be configured to work in alternate orders. In other words, any sequence or order of steps that may be described does not necessarily indicate a requirement that the steps be performed in that order. The steps of processes described herein may be performed in any order practical. Further, some steps may be performed simultaneously, in parallel, or concurrently.

While particular elements, embodiments, and applications of the present invention have been shown and described, it is understood that the invention is not limited thereto because modifications may be made by those skilled in the art, particularly in light of the foregoing teaching. It is therefore contemplated by the appended claims to cover such modifications and incorporate those features that come within the spirit and scope of the invention.

The invention claimed is:

1. A method of inhibiting spoilage of a volume of milk, the method comprising the step of:

immersing an anti-spoilage insert at least partially in the volume of milk for a predetermined period of time which is an effective time to inhibit spoilage, wherein the anti-spoilage insert comprises silver, wherein the silver is deposited on a substrate.

2. The method of claim 1, wherein the silver has a silver weight, wherein the substrate has a substrate weight, wherein the silver weight is at least 0.05% of the substrate weight.

3. The method of claim 2, wherein the substrate weight is at least 1 mg per mL of the volume of milk.

4. The method of claim 1, wherein the volume of milk is contained in a container, further comprising the step of attaching the anti-spoilage insert to the container.

5. The method of claim 1, wherein the substrate comprises fiberglass, plastic, paper, wood, wood-pulp, cellulose, silica, alumina, gelatin, agar, clay, carbon, non-woven material, woven material, fabric or any other material on which silver can be deposited.

6. The method of claim 1, wherein the silver comprises nanoparticles.

7. The method of claim 1, further comprising the step of removing the anti-spoilage insert from the volume of milk after the predetermined period of time has elapsed.

8. The method of claim 1, wherein the volume of milk comprises mammalian milk.

9. The method of claim 8, wherein the mammalian milk comprises human milk, cow milk, buffalo milk, goat milk, camel milk, sheep milk, or milk of any other mammal.

10. The method of claim 1, wherein the volume of milk comprises raw milk.

11. The method of claim 1, wherein the volume of milk comprises pasteurized milk, ultra-high temperature sterilized milk, or milk processed by any other preservation method.

12. A method for producing a milk anti-spoilage insert, the method comprising agitating a substrate in a precursor solution for at least 30 minutes, wherein the precursor solution comprises at least 0.01M silver nitrate;

drying the substrate;

heating the substrate at a temperature of at least 100° C. for at least 30 minutes; and heating the substrate at a temperature of at least 250° C. for at least 15 minutes.

13. The method of claim 12, wherein the substrate comprises fiberglass, plastic, paper, wood, wood-pulp, cellulose, silica, alumina, gelatin, agar, clay, carbon, non-woven material, woven material, fabric or any other material on which silver can be deposited.

14. The method of claim 12, further comprising the step of enclosing the substrate in an enclosure; wherein the enclosure allows the volume of milk to partially or wholly contact the substrate.

15. The method of claim 14, wherein the enclosure comprises a liquid permeable material.

16. The method of claim 15, wherein the liquid permeable material comprises non-woven fiber, woven fiber, fabric, paper, plastic or any other material that allows liquid to pass through the enclosure.

17. A method of inhibiting spoilage of milk, the milk having a volume, the method comprising the step of:

immersing a substrate comprising silver in milk for an effective time to inhibit spoilage;

wherein the substrate has a substrate weight, wherein the substrate weight is at least 1 mg per mL of the volume;

wherein the silver is deposited on the substrate, wherein the silver has a silver weight, wherein the silver weight is at least 0.05% of the substrate weight.

18. The method of claim 17, wherein the silver comprises nanoparticles.

* * * * *